(12) United States Patent
Havel et al.

(10) Patent No.: US 9,980,840 B2
(45) Date of Patent: May 29, 2018

(54) DELIVERY DEVICE WITH AN EXPANDABLE POSITIONER FOR POSITIONING A PROSTHESIS

(71) Applicant: Cook Medical Technologies LLC, Bloomington, IN (US)

(72) Inventors: William J. Havel, West Lafayette, IN (US); Matt Huser, West Lafayette, IN (US); Jarin Kratzberg, Lafayette, IN (US); Kimberly Ringenberger, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 281 days.

(21) Appl. No.: 14/925,597

(22) Filed: Oct. 28, 2015

(65) Prior Publication Data

US 2016/0158045 A1 Jun. 9, 2016

Related U.S. Application Data

(60) Provisional application No. 62/089,072, filed on Dec. 8, 2014.

(51) Int. Cl.
| | |
|---|---|
| *A61F 2/06* | (2013.01) |
| *A61F 2/966* | (2013.01) |
| *A61M 25/10* | (2013.01) |
| *A61M 25/00* | (2006.01) |
| *A61F 2/95* | (2013.01) |

(52) U.S. Cl.
CPC ....... *A61F 2/966* (2013.01); *A61F 2002/9511* (2013.01); *A61F 2002/9665* (2013.01); *A61F 2230/001* (2013.01); *A61F 2250/0003* (2013.01); *A61F 2250/0039* (2013.01); *A61M 25/0074* (2013.01); *A61M 2025/1047* (2013.01)

(58) Field of Classification Search
CPC ...... A61F 2/06; A61F 2/86; A61F 2/95; A61F 2/958; A61F 2/966
See application file for complete search history.

(56) References Cited

U.S. PATENT DOCUMENTS

| | | | |
|---|---|---|---|
| 4,950,227 | A | 8/1990 | Savin et al. |
| 5,108,416 | A | 4/1992 | Ryan et al. |
| 5,312,430 | A | 5/1994 | Rosenbluth et al. |
| 5,409,495 | A | 4/1995 | Osborn |
| 5,681,346 | A | 10/1997 | Orth et al. |
| 5,792,172 | A | 8/1998 | Fischell et al. |
| 5,916,263 | A | 6/1999 | Goicoechea et al. |
| 6,007,543 | A | 12/1999 | Ellis et al. |

(Continued)

OTHER PUBLICATIONS

European Search Report for corresponding EP Application No. 15275236.6, dated Mar. 2, 2017, 6 pages.

(Continued)

*Primary Examiner* — Victor Nguyen
(74) *Attorney, Agent, or Firm* — Brinks Gilson & Lione

(57) ABSTRACT

A prosthesis delivery device comprises a cannula having an expandable positioning device disposed at the proximal end thereof. A prosthesis is retained on the cannula distal of the expandable device. Expansion of the expandable device retains and centers the delivery device and the prosthesis carried thereon in the vessel and allows repositioning of the prosthesis without contacting the proximal end of the prosthesis with the vessel walls prior to deployment.

9 Claims, 10 Drawing Sheets

(56) References Cited

U.S. PATENT DOCUMENTS

| | | | |
|---|---|---|---|
| 6,174,316 B1 | 1/2001 | Tuckey et al. | |
| 6,419,685 B2 | 7/2002 | DiCaprio et al. | |
| 6,565,597 B1 | 5/2003 | Fearnot et al. | |
| 6,808,534 B1 | 10/2004 | Escano | |
| 7,695,487 B2 | 4/2010 | Peartree et al. | |
| 2001/0011187 A1 | 8/2001 | Pavcnik et al. | |
| 2003/0236570 A1 | 12/2003 | Cook et al. | |
| 2004/0034407 A1 | 2/2004 | Sherry | |
| 2004/0098079 A1* | 5/2004 | Hartley | A61F 2/95 623/1.11 |
| 2005/0273148 A1 | 12/2005 | Malher | |
| 2006/0149349 A1 | 7/2006 | Garbe | |
| 2006/0276872 A1* | 12/2006 | Arbefeuille | A61F 2/07 623/1.11 |
| 2008/0183280 A1 | 7/2008 | Agnew et al. | |
| 2010/0042121 A1 | 2/2010 | Schneider et al. | |
| 2011/0208290 A1 | 8/2011 | Straubinger et al. | |
| 2012/0004717 A1 | 1/2012 | Sanati et al. | |
| 2012/0130470 A1 | 5/2012 | Agnew et al. | |
| 2012/0191174 A1 | 7/2012 | Vinluan | |
| 2012/0197378 A1 | 8/2012 | Houser | |
| 2012/0222969 A1 | 9/2012 | Osborne et al. | |
| 2013/0338787 A1 | 12/2013 | Hopkins et al. | |
| 2014/0277341 A1 | 9/2014 | Havel et al. | |
| 2014/0277342 A1 | 9/2014 | Roeder et al. | |

OTHER PUBLICATIONS

Extended European Search Report for corresponding EP Appln. No. 15275236 dated Jun. 15, 2016, 7 pages.
Communication for corresponding EP Appln. No. 15275236 dated Nov. 25, 2016, 4 pages.

\* cited by examiner

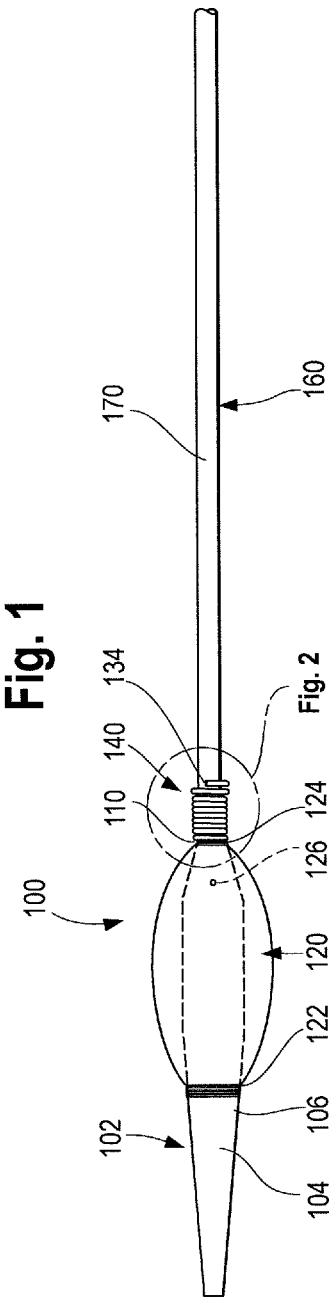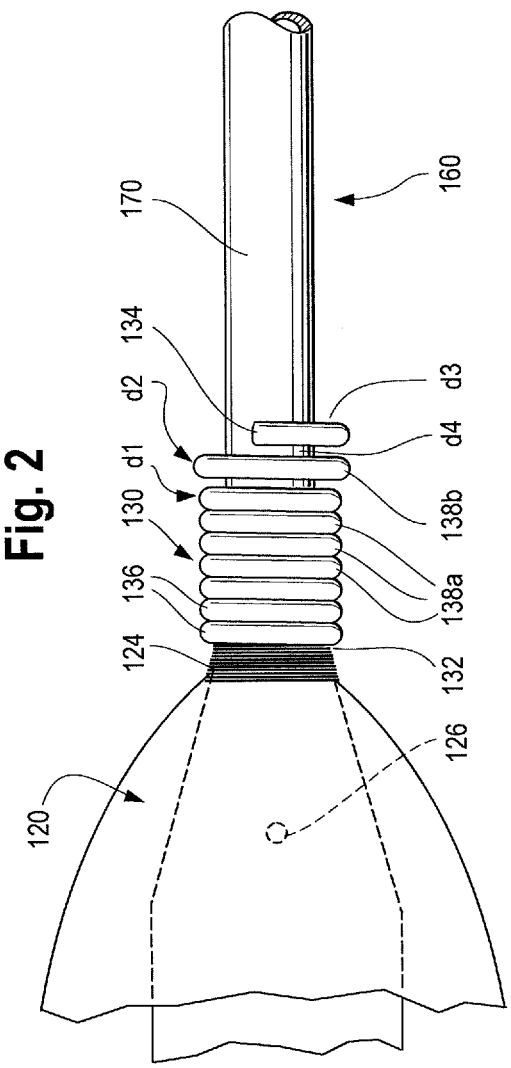

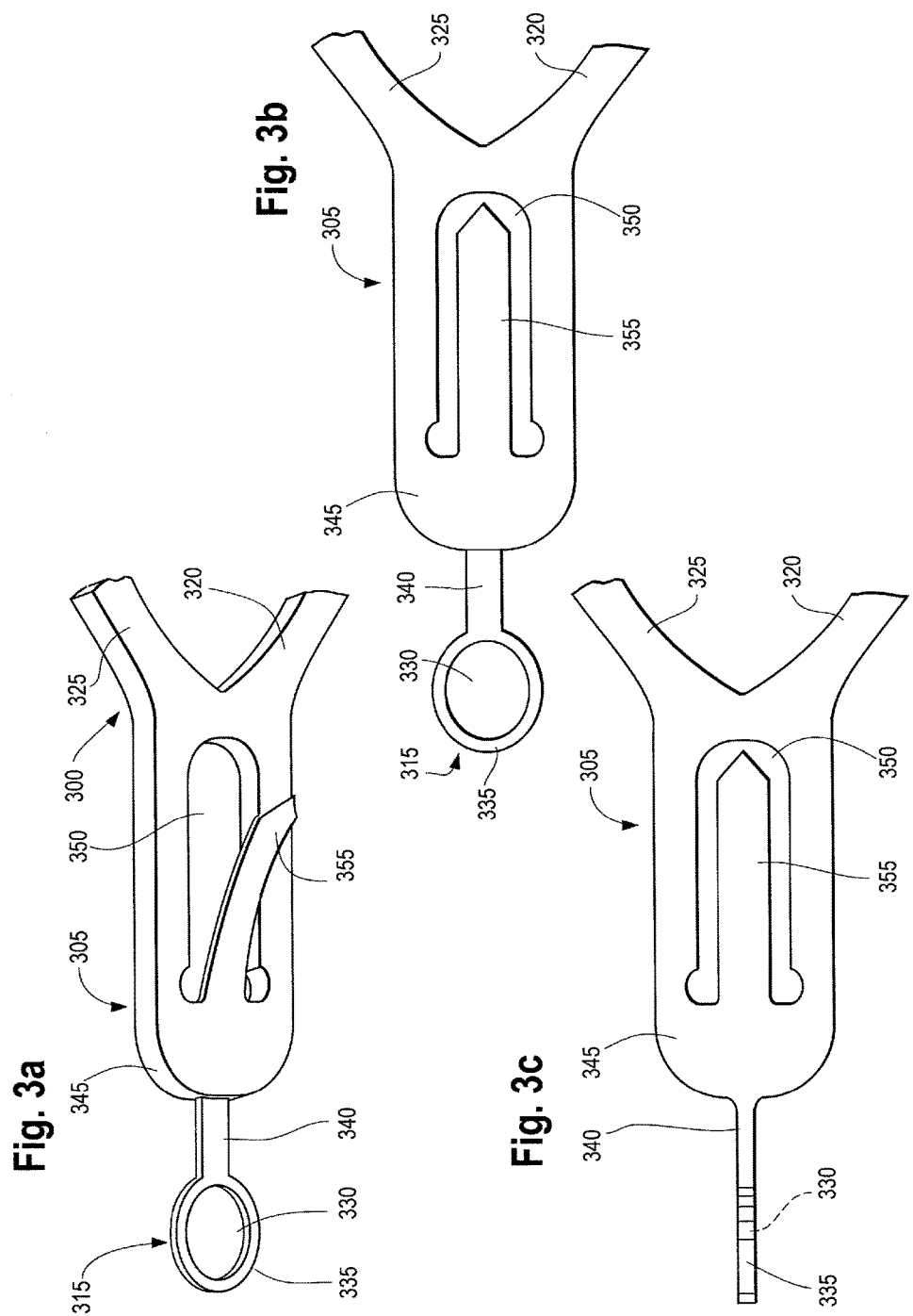

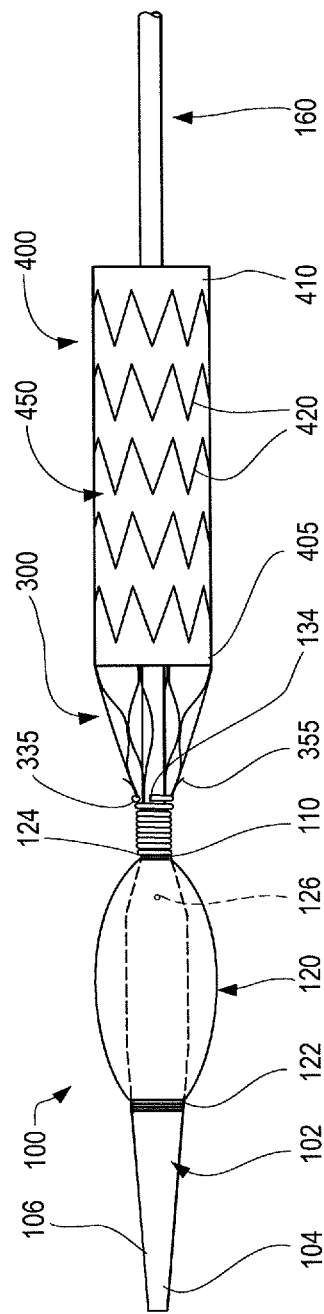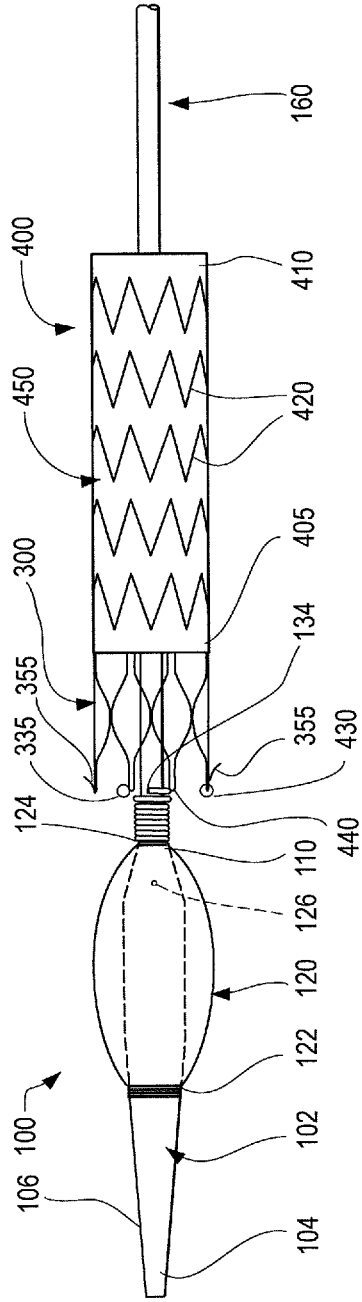

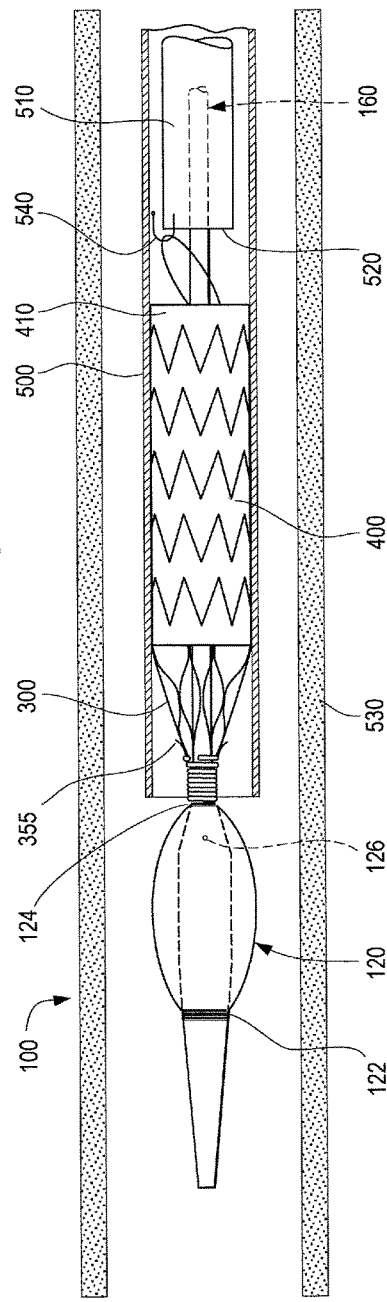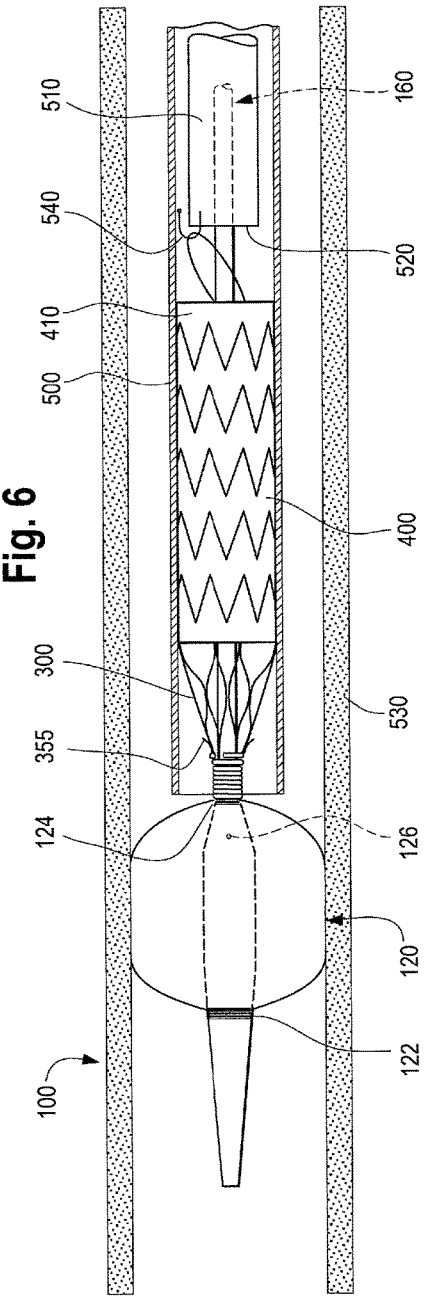

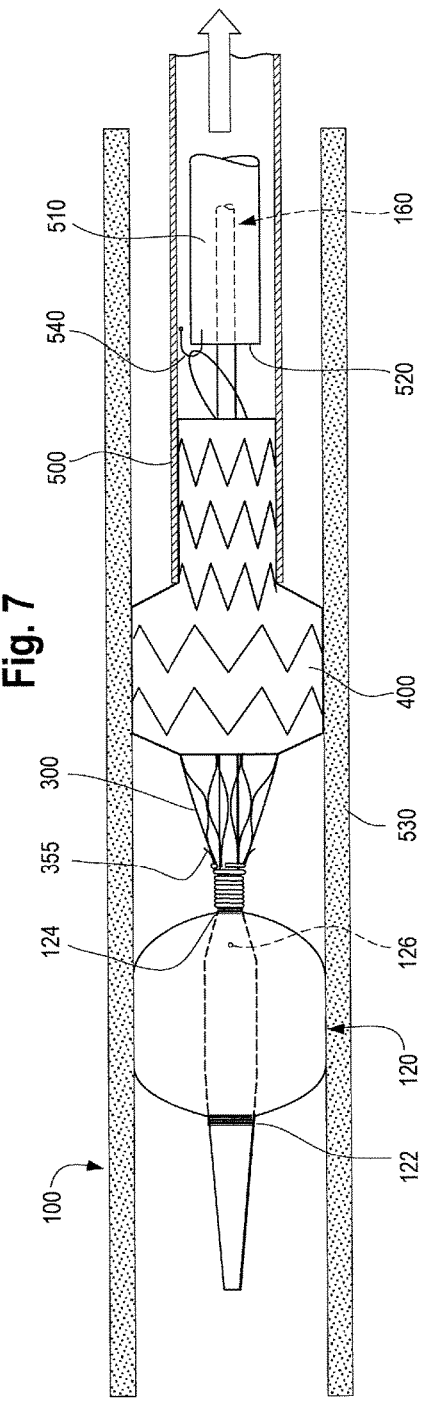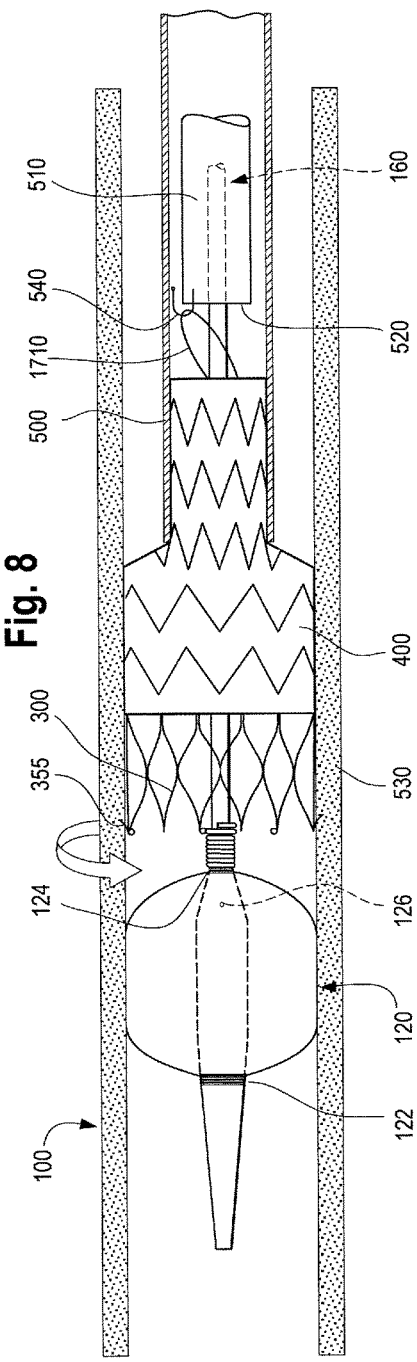

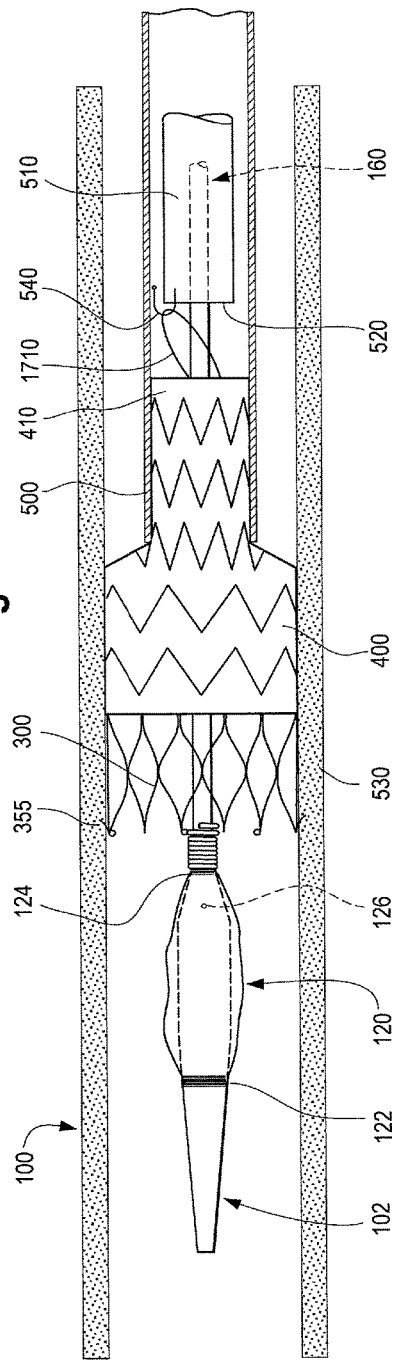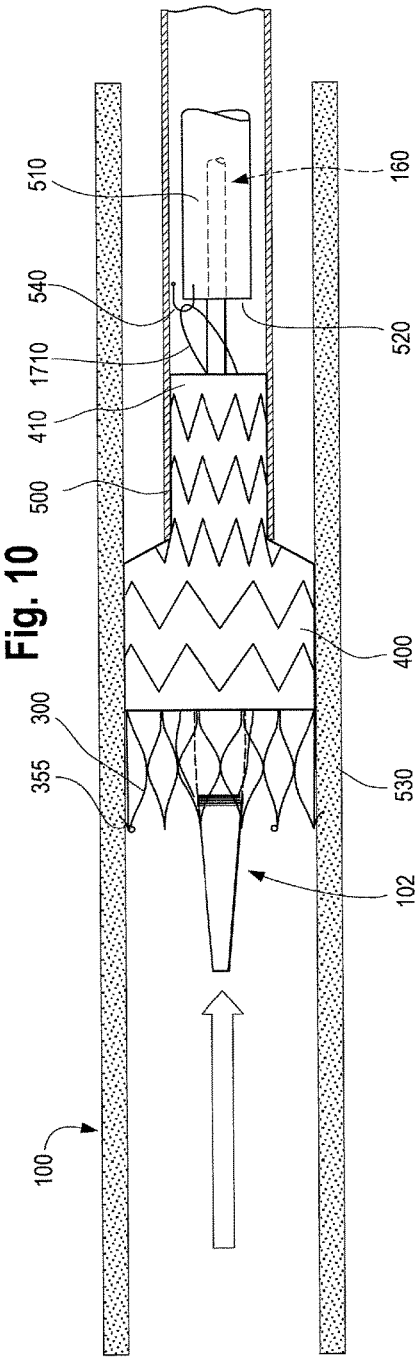

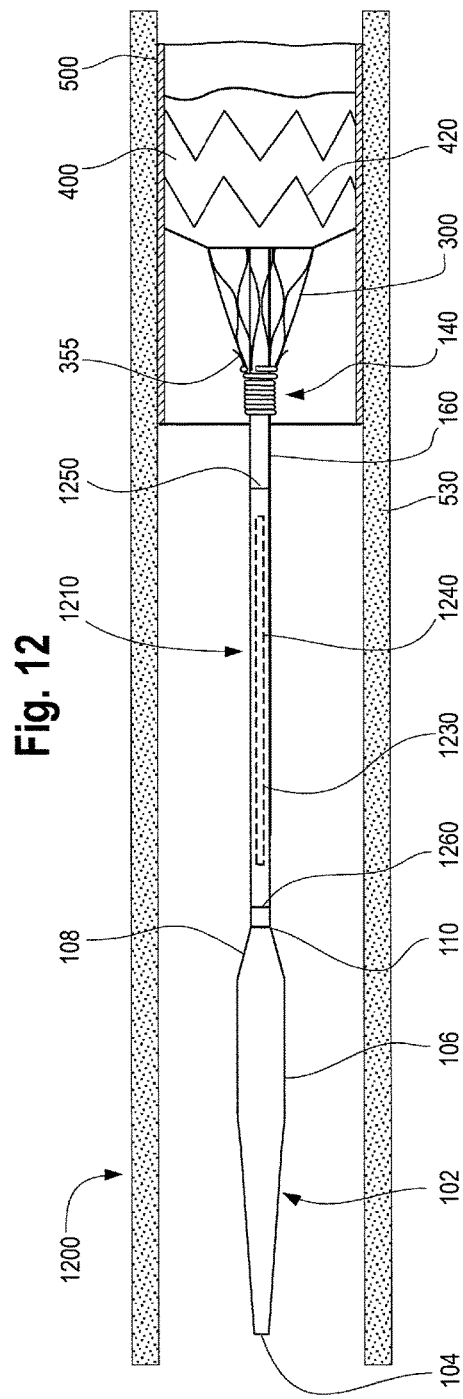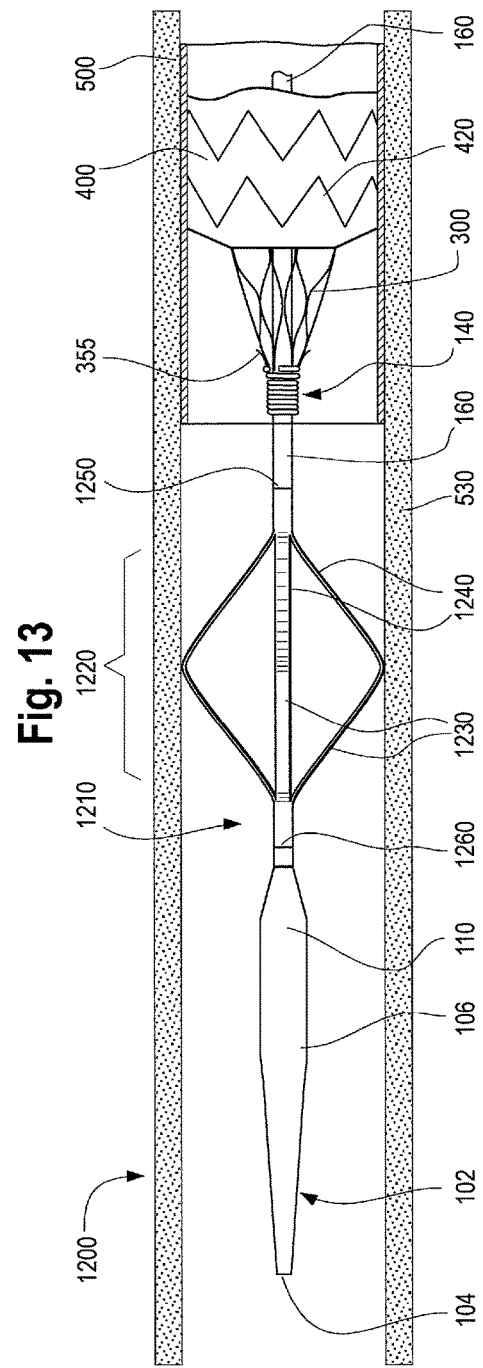

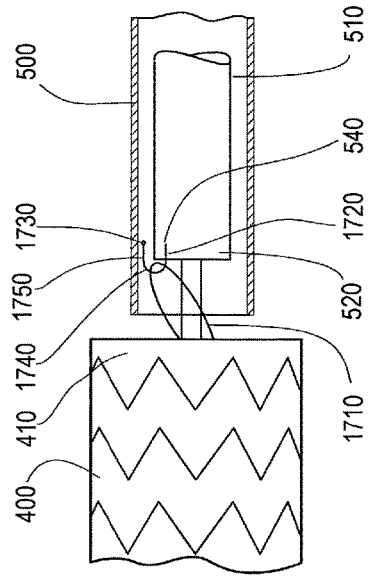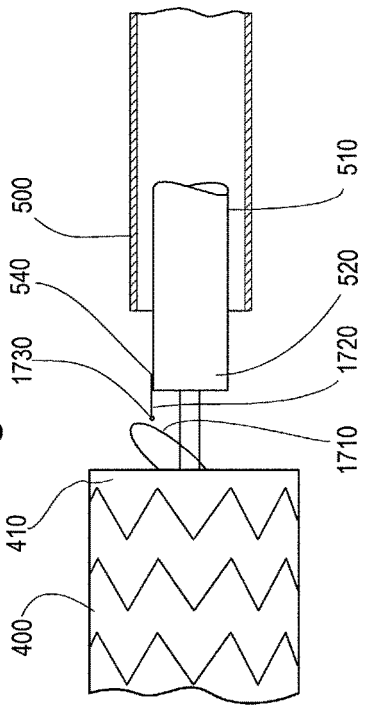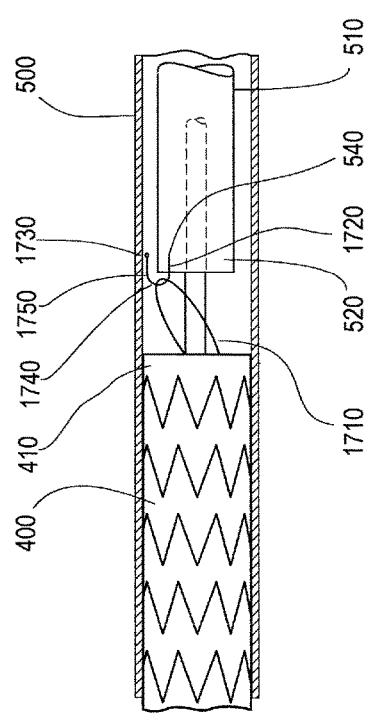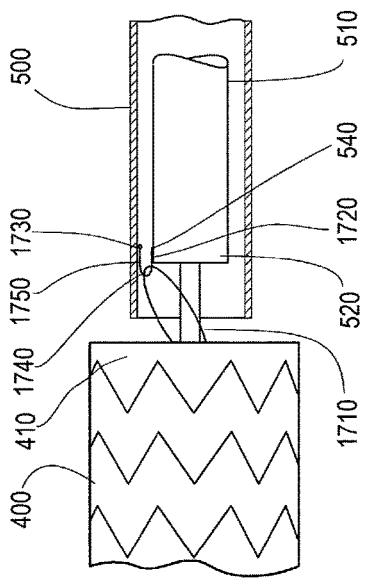

DELIVERY DEVICE WITH AN EXPANDABLE POSITIONER FOR POSITIONING A PROSTHESIS

RELATED APPLICATIONS

The present application claims the benefit of the filing date under 35 U.S.C. § 119(e) of Provisional U.S. Patent Application Ser. No. 62/089,072, filed Dec. 8, 2014, which is hereby incorporated by reference.

BACKGROUND

The present invention relates to delivery devices for prostheses, such as stents, grafts and stent grafts (collectively prostheses) in the vascular system of a patient. In particular, the invention relates to a prosthesis delivery device having an expandable positioner that allows centering and repositioning of a prosthesis in a vessel prior to deployment.

SUMMARY

A prosthesis delivery device is described. In one example, the delivery device comprises a delivery cannula having at least one lumen extending there through and a proximal end. A nose cone dilator is disposed at the proximal end of the delivery cannula and an opening is formed in a wall of the nose cone dilator. The opening is in flow communication with the cannula lumen. An expandable positioner is disposed about the opening formed in the wall nose cone dilator. The expandable positioner comprises a wall defining an interior space, wherein the interior space of the expandable positioner is in flow communication with the at least one cannula lumen via the opening formed in the wall of the nose cone. The positioner comprises a radially expanded condition and a radially contracted condition, such that flowing a fluid proximally through the at least one cannula lumen, through the opening formed in the wall of the nose cone dilator, and into the interior space of the positioner moves the positioner from the contracted condition to the expanded condition.

In another example, a prosthesis delivery device is described. The delivery device comprises a delivery cannula having a longitudinal axis and an expandable proximal region, wherein the expandable proximal region comprising a plurality of expandable wings. A prosthesis retention section is located on the delivery cannula distal to the expandable proximal region, and a retractable sheath disposed about the prosthesis. The expandable wings are expanded radially outwardly by urging together a proximal end and a distal end of the expandable proximal region along the longitudinal axis.

A method of delivering a prosthesis is also described. In one example, the method comprises introducing a delivery device into a vessel. The delivery device comprises a delivery cannula having at least one lumen extending there through and a proximal end, a nose cone dilator disposed at the proximal end of the delivery cannula, a radially expandable positioner disposed about a portion of the nose cone, a prosthesis carried on the delivery cannula distal to the radially expandable positioner and a retractable sheath disposed about the prosthesis. The method further comprises the steps of flowing fluid through the at least one lumen to expand the expandable positioner, positioning the delivery device in the vessel, retracting the sheath to expose at least a proximal end of the prosthesis, releasing the proximal end of a prosthesis from the delivery cannula and releasing the distal end of the prosthesis from the delivery cannula.

An alternative method of delivering a prosthesis is also described. The method comprises introducing a delivery device into a vessel. The delivery device comprises a delivery cannula having a first lumen extending there through and a proximal end, a nose cone dilator disposed at the proximal end of the delivery cannula, a radially expandable positioner disposed distally of the nose cone, a prosthesis carried on the delivery cannula distal to the radially expandable positioner and a retractable sheath disposed about the prosthesis. The method further comprises expanding the positioner to position the delivery device in the vessel, retracting the sheath to expose at least a portion of the prosthesis, releasing a proximal end of a prosthesis from the delivery cannula and releasing the distal end of the prosthesis from the delivery cannula.

BRIEF DESCRIPTION OF THE DRAWINGS

FIG. 1 is a side view of the proximal end of the prosthesis delivery device having a radially expandable positioner.

FIG. 2 is an enlarged view of the proximal end of the delivery device of FIG. 1.

FIG. 3a is an enlarged view of a proximal apex of a proximal end stent that may be coupled to the proximal end of the delivery device.

FIGS. 3b-c illustrate twisting of a portion of the proximal end stent of FIG. 3a.

FIG. 4a shows a side view of the delivery device of FIG. 1 having a radially expandable positioner and a prosthesis located just distal of the positioner.

FIG. 4b shows the device of FIG. 4a after release of the proximal end stent.

FIGS. 5-11 illustrate one example of a procedure for delivering a prosthesis with a delivery device having an expandable positioner to allow centering and repositioning of the prosthesis before deployment.

FIGS. 12-13 show an alternative example of a delivery device having an expandable positioner.

FIGS. 17a-d illustrate side views of the attachment of the distal end of a prosthesis to the delivery device.

DETAILED DESCRIPTION

Figure 11:
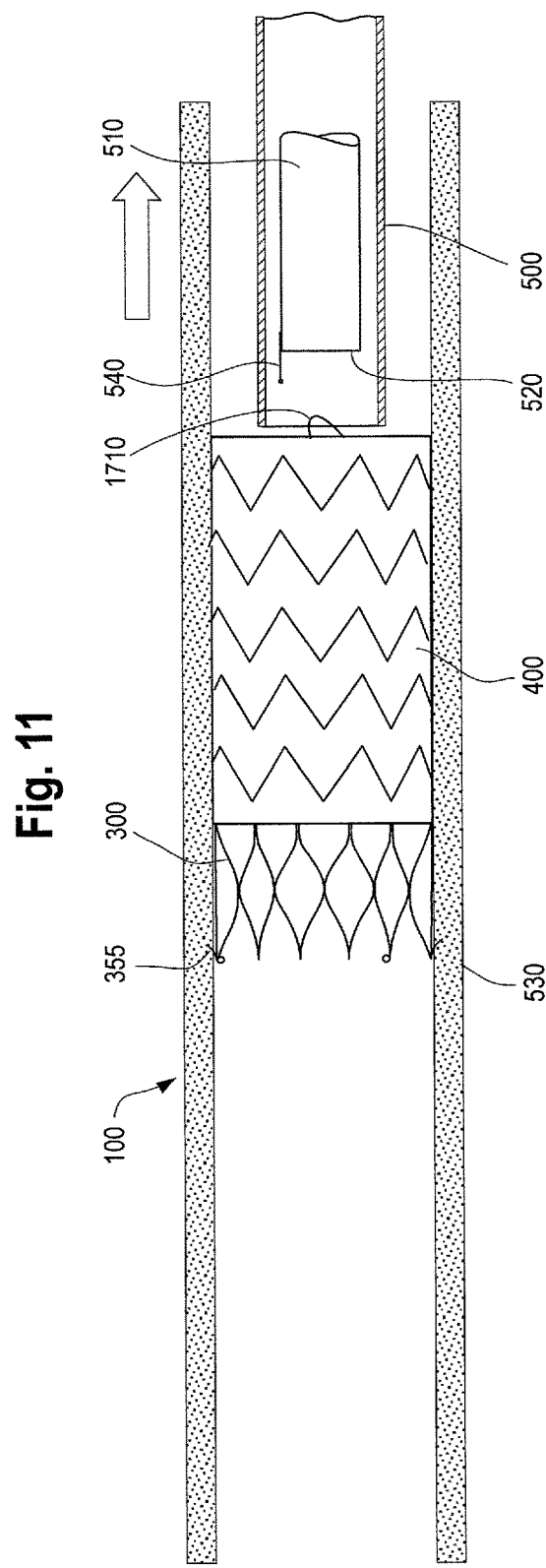

The embodiments described in this disclosure will be discussed generally in relation to deployment of prostheses, such as stents, grafts and stent grafts into a patient's vasculature, but the disclosure is not so limited and may be applied to other body vessels, organs or lumens.

In the present application, the term "proximal" refers to a direction that is generally closest to the heart during a medical procedure, while the term "distal" refers to a direction that is furthest from the heart during a medical procedure.

The term "stent graft" refers to a device that has a tubular body of biocompatible graft material and at least one stent fastened to the tubular body to define a lumen through the stent graft. The stent graft may be bifurcated and/or may include fenestrations, side arms, or the like. Other arrangements of stent grafts also are within the scope of this disclosure.

In one example, a delivery device is described that facilitates the positioning and centering of the device in a vessel prior to release and deployment of a prosthesis. In particular, the delivery device is operable to keep one or more anchoring structures located on a bare proximal stent from engaging with the vessel wall prior to deployment by retaining the proximal end of the delivery device in the center of the vessel. For example, the delivery device may include a balloon integrated into the flexible tip of the delivery device that can be inflated to retain the delivery device in the center of the vessel. In another example, the delivery device may include a malecot structure that can be expanded to retain the delivery device in the center of the vessel.

During the delivery process, the delivery device is first guided to a target location within the vasculature with a prosthesis retained on the proximal end of the delivery device. Once in position, the expandable positioner is expanded to retain the delivery device in the center of the vessel. The prosthesis remains attached to the proximal end of the delivery device, with the proximal stent retained radially inwardly on the delivery device. The expandable positioner, whether a balloon, malecot, or some other expandable structure, has a diameter that exceeds the diameter of any anchoring structures located on the proximal stent (such as barbs) so that the anchors are kept away from the vessel wall to prevent them from engaging the vessel, thus allowing the prosthesis to be adjusted or repositioned as needed. When the desired position is obtained, the expandable positioner can be returned to its unexpanded state and the prosthesis fully released at the target location.

The prosthesis can be retained on the delivery device through various types of attachment and release mechanisms. The proximal end attachment and release mechanism, as described in more detail below, may include a helix system that is shown and described in U.S. patent application Ser. No. 13/796,395, filed Mar. 12, 2013, which is incorporated by reference in its entirety herein. In another example, the proximal end attachment and release mechanism may include a trigger wire or other structure or diameter reducing tie(s) that releasably retains the proximal portion of the prosthesis on the delivery device before release.

The attachment and release mechanism that retains the distal end of the prosthesis on the delivery device may include a wireless medical device release mechanism that is shown and described in U.S. patent application Ser. No. 13/838,013, filed Mar. 15, 2013, which is incorporated by reference in its entirety herein. Other embodiments of exemplary distal end attachment and release mechanisms can similarly be found in U.S. patent application Ser. No. 13/835,877, filed Mar. 15, 2013, which is incorporated by reference in its entirety herein. In another embodiment, the distal end attachment and release mechanism may include a trigger wire or other structure that releasably retains the distal portion of the prosthesis on the delivery device before release.

FIGS. 1 and 2 illustrate the proximal end of a delivery device 100 having a cannula 160, a tapered nose cone 102 having a proximal tip 104, and an expandable device 120 disposed about the distal end 110 of the nose cone 102. The nose cone surface 106 presents a smooth tapered surface to facilitate entry into and movement through a body vessel. As shown in an enlarged view in FIG. 2, an exemplary stent proximal end attachment and release mechanism 140 (see FIG. 1) is disposed at or near the distal end 110 of the nose cone 102 and on the cannula 160. An expandable device 120 is disposed about the distal end 110 of the nose cone 102 and is attached to the nose cone 102 by seals on the proximal end 122 and distal end 124. In this non-limiting example, the proximal end 122 of the expandable device 120 and the distal end 124 of the expandable device 120 are secured to the outer surface of the nose cone 102 using a suitable mechanism, such as adhesives, bonding, heat sealing, and the like. This expandable device 120 is disposed over entrance port 126 which provides an entrance for the flow of fluid from the second lumen 1420 of FIG. 14 as described further below.

As shown in FIG. 2, the attachment and release mechanism 140 for the proximal stent comprises coiled member 130, having a proximal end 132, a distal end 134, and a plurality of turns 136 disposed there between. In a non-limiting example, the proximal end 132 of the coiled member 130 is secured to the outer surface 170 of the cannula 160 using a suitable attachment mechanism, such as a solder, weld, mechanical attachment, friction fit, crimp or combination thereof. Accordingly, the proximal end 132 of the coiled member 130 cannot move relative to the cannula outer surface 170 of cannula 160. The proximal end 132 of the coiled member 130 comprises a first diameter d1, which may be approximately the same diameter, or slightly greater than, an outer diameter of the cannula 160. The distal end 134 of the coiled member 130 may comprise a second diameter d2, which is greater than the first diameter d1 of the proximal end 132 of the coiled member 130. There is a separation or gap d3 between the distal end 134 of the coiled member 130 and the cannula outer surface 170 of the cannula 160, as seen in FIG. 2.

The plurality of turns 136 are divided into a proximal series of turns 138a, which have the first diameter d1, and a distal series of turns 138b, which have the second diameter d2. The proximal series of turns 138a may be disposed in close proximity or abutting one another, as depicted in FIG. 2. By contrast, the distal series of turns 138b may be spaced apart from one another a greater predetermined distance denoted by spacing d4.

Turning now to FIGS. 3a-c, one example of a portion of a bare proximal top stent 300 of a prosthesis 400 (FIGS. 4a-b) is shown. The proximal top stent 300 may be releasably engaged with the coiled member 130 of attachment and release mechanism 140 described above. This type of attachment system of the proximal stent to the delivery system is more fully described in U.S. application Ser. No. 13/796,395, filed Mar. 12, 2013, and in particular, with reference to FIGS. 6-8, which application is incorporated by reference in its entirety. The proximal end 305 of bare proximal top stent 300 includes at least one proximal apex 315 having a region comprising an aperture, opening or eyelet 330.

The eyelet 330 may be formed within a suture loop 335 that is disposed at the proximal end of a proximal extension segment 340. The proximal extension segment 340 extends in a proximal direction away from the end region 345, which end region 345 comprises an anchoring mechanism or structure for attaching or engaging the stent with a vessel wall, such as a barb 355 as shown in FIGS. 3a-c.

In one example, the suture loop 335 and the proximal extension segment 340 comprise a wall thickness that is less than a wall thickness of the end region 345 having the barb 355, as best seen in FIG. 3a. Advantageously, the reduced wall thickness of the suture loop 335 and the proximal extension segment 340 allows at least the suture loop 335 to twist circumferentially to facilitate loading of the proximal end 305 of the bare stent around the coiled member 130. In the non-limiting example shown, the suture loop 335 twists in a circumferential direction about 90 degrees between a first state shown in FIG. 3b and a second state shown in FIG. 3c. The suture loop 335 may twist greater than or less than 90 degrees as necessary or desired. Moreover, at least a portion of the proximal extension segment 340 may twist in the circumferential direction as the suture loop 335 is circumferentially twisted.

The proximal extension segment 340 provides longitudinal separation of the suture loop 335 housing the eyelet 330 from the end region 345 having the barb 355. Accordingly, when the eyelet 330 is threaded around the coiled member 130, the proximal extension segment 340 provides a longitudinal spacing that reduces the likelihood of entanglement between the coiled member 130 and the barb 355 formed in end region 345.

The proximal apex 315 shown in FIGS. 3a-3c may be provided on each and every proximal end 305 the bare proximal top stent 300. Alternatively, the proximal apex 315 may be provided on fewer than all of the proximal ends 305 of the bare proximal top stent 300, and the remaining proximal ends 305 may be provided with only barbs or similar vessel engaging structures such as the barb 355 pictured in FIGS. 3a-3c, or the remaining proximal ends 305 may comprise other features or structures.

In FIGS. 4a and 4b, an exemplary coupling of a stent graft 400 to a delivery device 100 is shown. The stent graft 400 has an uncoupled state in which the stent graft 400 is positioned coaxially over the cannula 160 with the proximal end 405 of the stent graft 400 longitudinally spaced from the distal end 134 of the coiled member 130. During assembly, one or more suture loops 335 that are coupled to the proximal ends or apices 430 of the bare proximal top stent 300 are threaded around the distal end 134 of the coiled member 130. Such coupling may be achieved by rotating the cannula 160 in a clockwise direction until the proximal end 405 of the bare proximal top stent 300 is sufficiently compressed in a radially inward direction, as depicted in FIG. 4a. As the gap d3 of FIG. 2 between the distal end 134 of the coiled member 130 and the cannula outer surface 170 permits positioning of the coiled member 130 through the suture loops 335 in a series of turns at the distal end 134 of the cannula 160. This type of attachment system of the proximal stent to the delivery system is more fully described in U.S. application Ser. No. 13/796,395, filed Mar. 12, 2013 which is incorporated herein by reference.

One or more suture loops 335 are further accommodated within the spacing d4 (FIG. 2) between the distal series of turns 138b. The suture loops 335 are preferably coupled to the coiled member 130 in a manner in which at least one suture loop 335 is positioned around at least one full turn of the distal series of turns 138b and preferably around at least 1.5 turns at the distal end 134 of coiled member 130, thereby reducing the likelihood of inadvertent uncoupling of the at least one suture loop 335 from the coiled member 130. The coupling shown in FIG. 4a secures the bare proximal top stent 300 to the cannula 160 via the coiled member 130 in a manner that may subsequently facilitate insertion of a subassembly comprising the cannula 160 and the stent graft 400 into a sheath 500. As described further below, the sheath 500 is configured to radially inwardly restrain the stent graft 400 for delivery to a target site within a patient's anatomy.

The suture loops 335 may be coupled to every other proximal end or apex 430 as shown in FIGS. 4a-b to restrain the bare proximal top stent 300 and hold it in a radially inward or compressed configuration having a reduced profile during delivery. In one example, the suture loops 335 are not coupled to the second proximal ends or apices 440, which may comprise barbs. By restraining the alternating proximal ends or apices 430 using the suture loop(s) 335 coupled to the coiled member 130, the second proximal apices 440 may be indirectly pulled in a radially inward direction during delivery. In other words, the configuration of the bare proximal top stent 300 facilitates the indirect compression of the adjacent second proximal apices 440. Since only selected ones of the proximal ends or apices are restrained during delivery, the number of suture loop(s) 335 may be reduced.

The above description of the proximal end attachment and release mechanism 140 which comprises at least one coiled member 130 to releasably engage the proximal bare stent is not intended to be limiting, and one of skill would recognize that the delivery device may be provided with one or more alternative mechanisms to releasably engage the proximal top stent 300 and/or the stent graft 400 during delivery and deployment, including but not limited to one or more trigger wires, diameter reducing ties and other attachment mechanisms that would be recognized by one of skill in the art.

FIGS. 5-11 illustrate one example of the delivery device 100 in use, and more specifically, the positioning and centering of the delivery device 100 and subsequent release of the stent graft 400 within a vessel. As shown in FIG. 5, the stent graft 400 is loaded on the delivery device 100 and compressed by sheath 500. In operation, the user guides the delivery device 100 to a target location within the patient's body. Once the delivery device 100 is in a desired position, the operator expands the expandable device 120 to retain and stabilize the delivery device 100 in the center of the vessel lumen 530 as shown in FIG. 6.

Figure 14:
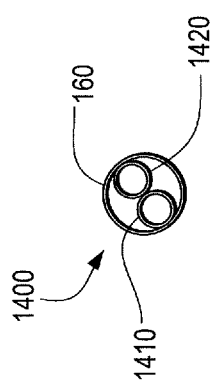
FIG. 14 is a cross-sectional view of the cannula used in the delivery device of FIGS. 1-2 and 4-11.

In one non-limiting example, the expandable device 120 may include an inflatable structure or balloon. The cannula 160 may include a first lumen 1410 and at least a second lumen 1420 that run parallel to each other through the center of the cannula 160 as shown in FIG. 14, wherein the second lumen 1420 provides for the flow of fluid and/or gas to allow inflation or deflation of the expandable device 120. To inflate the expandable device 120, fluid flows in a proximal direction through the second lumen 1420, through the entrance port 126 on the nose cone 102 and into the expandable device 120. Fluid is contained in the expandable device 120 by attachments to nose cone 102 at the proximal end 122 and distal end 124 and allows the expandable device 120 to inflate. To deflate the expandable device 120, fluid exits out the expandable device 120 through the entrance port 126 on the nose cone 102 and into the second lumen 1420 where it travels in a distal direction away from the expandable device 120.

In further operation, the operator then withdraws the sheath 500 in the distal direction as indicated by the arrow shown in FIG. 7 so that the bare proximal top stent 300 is at least partially exposed. In this position, the barbs 355 are kept away from the vessel lumen 530, allowing the user to reposition and adjust the longitudinal position of the stent graft 400 as needed prior to final deployment and/or release. When the desired position is obtained, the cannula 160 may be rotated (such as in a clock-wise direction as shown by the arrow in FIG. 8) until the at least one suture loop 335 is uncoupled from the coiled member 130 (i.e. in a reverse manner from which the at least one suture loop 335 was coupled to the coiled member 130). The bare proximal top stent 300 then may be deployed as shown in FIGS. 4a-b and 8. In an alternative embodiment, the proximal end 405 of the stent graft 400 may be radially restrained through the use of trigger wires that can be contained in at least one of the first and second lumens, and preferably, in the first lumen 1410 of the cannula 160 of FIG. 14.

FIGS. 9-11 demonstrate the continued operation of the delivery device 100 to release the distal end 410 of the stent graft 400. The distal end 410 of the stent graft 400 is attached to the delivery device 100 by way of at least one distal attachment and release mechanism 540 on positioner 510 which engages a corresponding element at the distal end 410, such as a looped portion 1710. However, as previously mentioned, the distal end of the stent graft may be releasably coupled to the delivery device by other acceptable mechanisms including one or more trigger wires, diameter reducing ties or combinations thereof. As shown in FIG. 9, the expandable device 120 is deflated as the fluid contained in the expandable device 120 exits through the entrance port 126 through the second lumen 1420 in a distal direction. The sheath 500 is then fully withdrawn and removed from the stent graft in a distal direction as shown by the arrow in FIG. 10. The full withdrawal of the sheath 500 exposes the distal end 410 of the stent graft 400 as shown in FIG. 11. The distal end 410 of the stent graft 400 is then fully released by releasing the looped portion 1710 from the distal attachment and release mechanism 540 as also shown in FIG. 11.

FIGS. 17a-d are enlarged side views of the distal end of a prosthesis with an exemplary distal attachment and release mechanism. As shown there, the sheath 500 is transparent to allow objects covered by the sheath 500 to be visible. The sheath 500 may actually be opaque or transparent or a combination thereof. Positioner 510 has a releasable distal attachment and release mechanism 540 at the proximal end 520. In this example, the attachment and release mechanism comprises a capture wire 1720 on the positioner 510 which is bent to engage a looped portion 1710 or other corresponding structure or configuration at the distal end 410 of the stent graft 400.

While the sheath 500 is disposed over the capture wire 1720, the capture wire 1720 is prevented from straightening. A close fit of the sheath 500 over the positioner 510 and capture wire 1720, as shown in 17b, prevents the looped portion 1710 from releasing or becoming detached from the capture wire 1720 while the sheath 500 is positioned over it. At least a portion of the capture wire 1720 is affixed to the positioner 510. An unattached section 1750 of the capture wire 1720 may be free and not attached to the positioner 510. For example, the capture wire 1720 may include one or more bends in the unattached section 1750 when the sheath 500 covers the capture wire 1720. In the case of a single bend, the bend may be approximately 180 degrees. The unattached section of the capture wire 1720 is held in the bent position by the presence of the sheath 500 where the unattached section 1750 is prevented from straightening out and removing the bend 1740.

The unattached section 1750 of the capture wire 1720 may include an atraumatic portion 1730 which may prevent damage to a vessel wall or body cavity if the unattached section 1750 of the capture wire 1720 contacts the vessel wall or body cavity. The atraumatic portion 1730 may take any shape that prevents or minimizes damage to a vessel wall or body cavity including, for example, a rounded ball, curved segment, curved end, or cushioned area.

The capture wire 1720 may be composed of any material capable of deforming and later returning to its un-deformed shape, such as bending and later straightening, without any external force applied. The capture wire 1720 may consist of, for example, nitinol or polypropylene filament. The length, thickness, and flexibility of the capture wire 1720 may be varied depending on the application. For example, a thicker or less flexible capture wire 1720 may be used if the looped portion 1710 applies a relatively large force to the capture wire 1720. A longer capture wire 1720 may be used if the diameter of looped portion 1710 is relatively large or if the space between the proximal end 520 of the sheath 500 is relatively large.

FIG. 17d shows the sheath 500 withdrawn from the capture wire 1720. The capture wire 1720 may return to its un-deformed or unbent shape automatically upon removal of the sheath 500. For example, removal from the sheath from over the capture wire 1720 permits the capture wire 1720 to be relieved from its bent shape and release loop 1710, consequently releasing the distal end 410 of the prosthesis. After the distal end 410 is released, the device 100 may be removed from the prosthesis and the body vessel.

FIGS. 12, 13, and 15-16 illustrate another example of an expandable delivery device 1200. Like numbers denote similar features to that previously described. FIG. 12 provides an illustration of the expandable delivery device 1200 before expansion, comprising cannula 160, a nose cone 102 having a proximal tip 104 and the proximal end attachment and release mechanism 140 with attached stent graft 400. Nose cone 102 has a reverse distal taper 108 at its distal end 110. The nose cone surface 106 presents a smooth tapered surface to facilitate entry into and movement through a body vessel. An expandable device 1210 is located at the proximal end of the cannula 160. The expandable device 1210 is distal to the nose cone 102 but proximal to the proximal end attachment and release mechanism 140. In one example, the expandable device 1210 comprises a malecot or similar structure that may include expandable wings, ribs, walls, baffles or a combination thereof. As shown specifically in FIGS. 12 and 13, the malecot has an expandable region 1220 defined between the proximal end or circumference 1260 and the distal end or circumference 1250. The expandable device 1210 includes generally parallel slits 1230 that define lateral margins of malecot wings 1240. FIG. 13 illustrates the deployment of the expandable region 1220. The expandable region 1220 is deployed by urging the proximal circumference 1260 and distal circumference 1250 of the expandable region 1220 towards each other which causes the central region of the malecot wings 1240 to expand radially outwardly.

Figure 16:
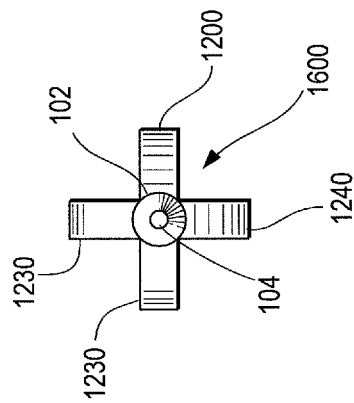
FIG. 16 is front view of the proximal end of the delivery device of FIGS. 12-13.
Figure 15:
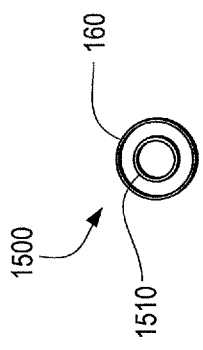
FIG. 15 is a cross-sectional view of the cannula used in the delivery device of FIGS. 12-13.

FIG. 15 illustrates one embodiment of a cross-sectional view of the cannula 160 used in the expandable delivery device 1200. An inner cannula 1510 is disposed within cannula 160 and is attached to the distal end 110 of the nose cone 102. In this embodiment, the expandable region 1220 is deployed by withdrawing the inner cannula 1510 in a distal direction relative to the cannula 160 which brings the proximal and distal ends 1260, 1250 closer together. In another embodiment, the expandable delivery device 1200 does not have an inner cannula 1510 and the expandable region 1220 is instead deployed by withdrawing a trigger wire (not shown) that is attached to the proximal end of the cannula 160. FIG. 16 shows a front view of the proximal end of expandable delivery device 1200 when the expandable malecot region 1220 is deployed.

Like the expandable device or balloon 120 described above, the expandable region 1220 retains and stabilizes the delivery device 100 in the center of the vessel lumen 530. This facilitates the positioning of the stent graft 400 as necessary. Once the stent graft 400 is deployed, the expandable delivery device 1200 can be withdrawn through the stent graft 400 by first moving the inner cannula 1510 in a proximal direction to pull the malecot wings 1240 radially inwardly such that the malecot device 1210 is flattened in a more slender profile for easy removal from the vessel.

An expandable positioning structure 120, 1200, which facilitates centering of the delivery device 100, achieves several advantages, including, without limitation, providing the user with more control in achieving accurate deployment of the prosthesis within a tortuous deployment zone. In one non-limiting example, providing the delivery device 100 with an expandable structure facilitates the centering of the proximal end of the delivery device and the proximal bare stent of the stent graft prior to deployment in a vessel lumen. In doing so, any anchoring structures such as barbs are prevented from prematurely engaging with a vessel wall, thus allowing the user to reposition the stent graft prior to its final release from the delivery device. Further, the expandable structure can also serve to expand the seal stents located, for example, in the body of the prosthesis, which would eliminate the need to re-insert another inflatable structure, such as a balloon, after implantation to fully expand the implanted prosthesis.

While particular elements, embodiments, and applications of the present invention have been shown and described, it is understood that the invention is not limited thereto because modifications may be made by those skilled in the art. It is therefore contemplated by the appended claims to cover such modifications and incorporate those features which come within the spirit and scope of the invention.

The invention claimed is:

1. A prosthesis delivery device comprising:
   a delivery cannula having at least one lumen extending there through and a proximal end;
   a nose cone dilator disposed at the proximal end of the delivery cannula, and an opening formed in a wall of the nose cone dilator, wherein the opening is in flow communication with the at least one cannula lumen;
   an expandable positioner disposed about the opening formed in the wall of the nose cone dilator, the expandable positioner comprising a wall defining an interior space, wherein the interior space of the expandable positioner is in flow communication with the at least one cannula lumen via the opening formed in the wall of the nose cone, wherein the positioner comprises a radially expanded condition and a radially contracted condition; and
   wherein flowing a fluid proximally through the at least one cannula lumen, through the opening formed in the wall of the nose cone dilator, and into the interior space of the positioner moves the positioner from the contracted condition to the expanded condition.

2. The delivery device of claim 1 wherein the expandable positioner comprises an inflatable device.

3. The delivery device of claim 2 wherein the at least one lumen is in flow communication with the inflatable device.

4. The delivery device of claim 1 wherein the expandable positioner comprises a balloon.

5. The delivery device of claim 1 wherein the expandable positioner comprises a proximal end and a distal end, and wherein the proximal and distal ends of the positioner are secured to an outer surface of the nose cone dilator.

6. The delivery device of claim 1 further comprising a prosthesis carried on the delivery cannula.

7. The delivery device of claim 6 wherein the prosthesis comprises a stent graft comprising a proximal bare stent.

8. The delivery device of claim 7 wherein the proximal bare stent comprises at least one anchoring mechanism configured to engage a vessel wall.

9. The delivery device of claim 8 wherein the at least one anchoring mechanism of the bare stent is prevented from engaging a vessel wall when the positioner is in an expanded configuration.

* * * * *